(12) United States Patent
Wagner et al.

(10) Patent No.: US 10,117,627 B2
(45) Date of Patent: Nov. 6, 2018

(54) SYSTEM AND METHOD TO MAINTAIN ENGAGEMENT OF GEARS FOR X-RAY IMAGING SYSTEM

(71) Applicant: General Electric Company, Schenectady, NY (US)

(72) Inventors: Grant Richard Wagner, Milwaukee, WI (US); Curt Allen Zimmerman, Neosho, WI (US); Matthew Jason Evangelist, Lake Mills, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 247 days.

(21) Appl. No.: 15/341,679

(22) Filed: Nov. 2, 2016

(65) Prior Publication Data
US 2018/0116616 A1 May 3, 2018

(51) Int. Cl.
*A61B 6/00* (2006.01)
*F16H 57/12* (2006.01)
*A61B 6/03* (2006.01)

(52) U.S. Cl.
CPC ............ *A61B 6/4435* (2013.01); *A61B 6/032* (2013.01); *A61B 6/037* (2013.01); *A61B 6/4417* (2013.01); *F16H 57/12* (2013.01); *F16H 2057/126* (2013.01)

(58) Field of Classification Search
None
See application file for complete search history.

(56) References Cited

U.S. PATENT DOCUMENTS

| 3,808,906 | A | 5/1974 | Bowers | |
|---|---|---|---|---|
| 4,338,853 | A | 7/1982 | Neumeyer | |
| 2001/0055362 | A1* | 12/2001 | Takanashi | A61B 6/035 378/15 |
| 2016/0287197 | A1* | 10/2016 | Risher-Kelly | A61B 6/4435 |

* cited by examiner

*Primary Examiner* — Hoon Song
(74) *Attorney, Agent, or Firm* — Fletcher Yoder, P.C.

(57) ABSTRACT

An X-ray imaging system includes a gantry, rotatable about an axis of rotation, a radiation source mounted on the gantry and configured to emit radiation, and one or more detectors configured to detect the emitted radiation. The gantry includes a gear assembly coupled to a motor to enable rotation of the gantry, wherein the gear assembly comprises a gantry gear. The gantry includes an encoder for detecting position of the gantry, wherein the encoder comprises an encoder gear meshed with the gantry gear. The gantry also includes a gear re-engagement assembly configured to couple to the encoder and to force the encoder gear into correct engagement with the gantry gear when the encoder gear becomes disengaged from the gantry gear. As such, the gear re-engagement assembly keeps engagement of the encoder gear and the gantry gear to maintain the important gantry position tracking.

20 Claims, 4 Drawing Sheets

SYSTEM AND METHOD TO MAINTAIN ENGAGEMENT OF GEARS FOR X-RAY IMAGING SYSTEM

BACKGROUND

The subject matter disclosed herein relates to imaging systems, and more particularly, to a re-engagement assembly to re-engage disengaged gear teeth back to correct engagement within a gantry of an imaging system.

In computed tomography (CT) or positron emission tomography-computed tomography (PET/CT), a CT scanner or combined PET/CT scanners are included in a gantry, where responses of a subject of interest to some specific exposure, such as X-ray radiation and/or gamma-ray radiation, can be detected for imaging. A gantry driving mechanism, such as motor(s) and gear(s), enables the gantry to rotate and/or move with respect to the subject of interest to obtain images. As such, gear teeth positioning is vital to CT and/or PET/CT imaging, where the location and/or rotation is being constantly tracked, and any misalignment and/or disengagement of the gear teeth may cause issues. For example, when gear interfaces are exposed to vibrations (e.g., seismic event) the gear teeth may jump (e.g., gear teeth disengage from proper meshing and/or skip teeth) and lose the valuable positioning (e.g., important position).

BRIEF DESCRIPTION

In accordance with a first embodiment, an X-ray imaging system includes a gantry, rotatable about an axis of rotation, a radiation source mounted on the gantry and configured to emit radiation, and one or more detectors configured to detect the emitted radiation. The gantry includes a gear assembly coupled to a motor to enable rotation of the gantry, wherein the gear assembly comprises a gantry gear. The gantry includes an encoder for detecting position of the gantry, wherein the encoder comprises an encoder gear meshed with the gantry gear. The gantry also includes a gear re-engagement assembly configured to couple to the encoder and to force the encoder gear into correct engagement with the gantry gear when the encoder gear becomes disengaged from the gantry gear.

In accordance with a second embodiment, a gear re-engagement system for a gantry of an X-ray imaging system includes a biasing member and a counter weight coupled to the biasing member. The counter weight is configured to spring load the biasing member. The counter weight is configured to couple to an encoder within the gantry and to force an encoder gear into correct engagement with a gantry gear within the gantry when the encoder gear becomes disengaged from the gantry gear.

In accordance with a third embodiment, a method for correcting gear jumping in a gantry of an X-ray imaging system includes coupling a gear re-engagement assembly to an encoder within an enclosure of the gantry. The method includes rotating the gantry about an axis of rotation based on a motor-driven gear assembly, which includes a gantry gear, wherein the gantry gear is correctly engaged with an encoder gear of the encoder. The method includes subjecting the gantry to vibration such that the encoder gear becomes disengaged from the gantry gear. The method also includes forcing the disengaged encoder gear into correct engagement with the gantry gear via the gear re-engagement assembly by contacting a spring-loaded biasing member of the gear re-engagement assembly with a wall of the enclosure.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Gear teeth positioning is vital to medical imaging applications that include a gantry that utilizes one or more gear assemblies (e.g., encoder gear, gantry gear) where location and/or rotation is being constantly tracked by multiple sensors simultaneously, and any misalignment and/or disengagement of the gear teeth can cause issues. When gear interfaces (e.g., interfaces between an encoder gear and a gantry gear) are exposed to vibrations (e.g., seismic event) the teeth may jump and lose the valuable positioning. The present disclosure provides for a gear re-engagement assembly (or gear engagement maintenance assembly) configured to couple to a CT or PET/CT gantry and ensure appropriate meshing (e.g., correct engagement) between an encoder gear and a gantry gear when the CT or PET/CT imaging system is subjected to vibration (e.g., seismic event). By way of example, the gear re-engagement assembly may include a bias member, which only becomes active at an instance that gear disengagement occurs (e.g., upon sufficient vibrations, seismic event), to force the disengaged gear back to its correctly engaged position. The bias member may be a spring-loaded bias member configured to exert a biasing force on a disengaged gear (e.g., jumping gear, skipping teeth, disengaged gears) to force the gear back to proper engagement or meshing. As a result, the gear re-engagement assembly does not interfere with operation of the CT or PET/CT imaging system and only becomes active if gear disengagement occurs (e.g., upon sufficient vibrations, seismic event).

Figure 1:
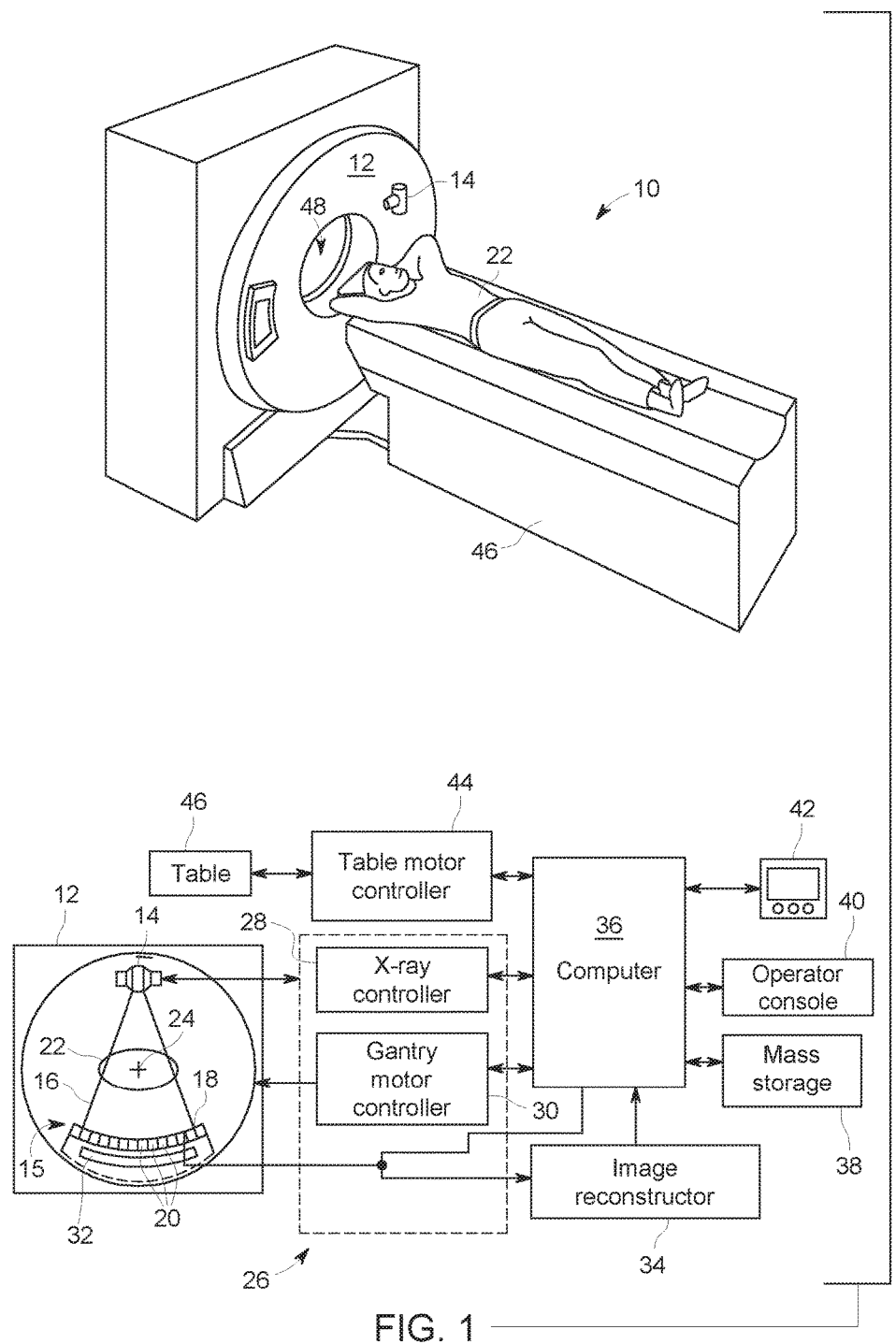
FIG. 1 is a combined pictorial view and block diagram of a CT or PET/CT imaging system, in accordance with an aspect of the present disclosure.

With the foregoing in mind and referring to FIG. 1, a CT imaging system 10 is shown as including a gantry 12. Gantry 12 has an X-ray source 14 that projects a beam of X-rays 16 toward a detector assembly 15 on the opposite side of the gantry 12. The detector assembly 15 includes a collimator assembly 18, a plurality of detector modules 20 (e.g., each having a detector array), and data acquisition systems (DAS) 32. The collimator assembly 18 may include a plurality of collimator modules integrated with components of the detector modules 20 (e.g., scintillator). The plurality of detector modules 20 detect the projected X-rays that pass through a medical patient 22, and DAS 32 converts the data to digital signals for subsequent processing. Each detector module 20 in a conventional system produces an analog electrical signal that represents the intensity of an impinging X-ray beam and hence the attenuated beam as it passes through the patient 22. During a scan to acquire X-ray projection data, gantry 12 and the components mounted thereon rotate about a center of rotation 24.

Rotation of gantry 12 and operation of the X-ray source 14 are governed by a control mechanism 26 of the CT imaging system 10. The control mechanism 26 includes an X-ray controller 28 that provides power and timing signals to the X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves portions of patient 22 through a gantry opening 48. It should be noted that although the illustrated embodiment depicts a CT imaging system, the CT imaging system 10 may be a combined PET/CT imaging system, including combined PET/CT scanners (e.g., X-ray and gamma-ray sources, detector modules, etc.) and computer aids in creating images from data obtained by the combined PET/CT scanners.

Figure 2:
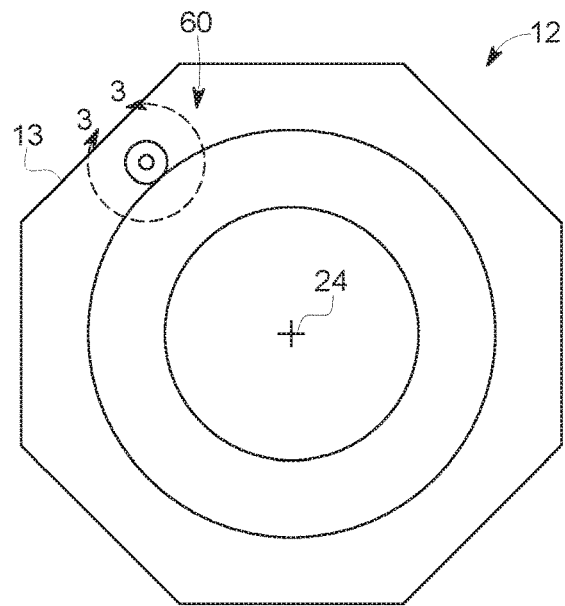
FIG. 2 is a perspective view of a gantry of the CT or PET/CT imaging system of FIG. 1, in accordance with an aspect of the present disclosure.

FIG. 2 is a perspective view of an embodiment of the gantry 12 of the CT imaging system 10. The gantry 12 includes an enclosure or a housing 13 (e.g., a wall, a bearing bracket), and within the enclosure 13, a gear assembly 60 coupled to the gantry motor controller 30 to enable rotation of the gantry 12 and the components mounted thereon about the center of rotation 24. The gear assembly 60 includes an encoder to track rotation and/or position of the gantry 12. For example, the encoder may measure the instantaneous angle of the gantry 12, and signal representing the rotational angle may be fed to the gantry motor controller 30 and/or the computer 36. Further, the gear assembly 60 includes a gear re-engagement assembly 61 within the enclosure 13 to ensure correct meshing of gears as will be discussed in FIG. 3.

Figure 3:
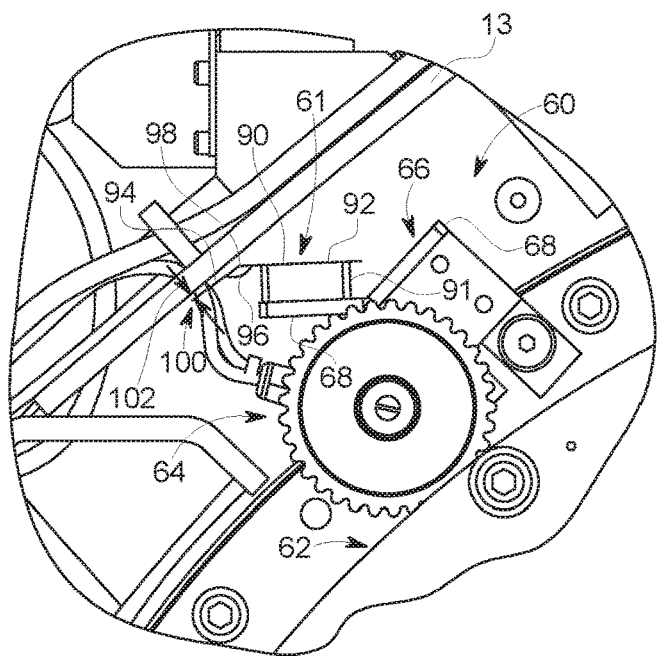
FIG. 3 is a partial cutaway view of the gantry of FIG. 2, taken within line 3-3, illustrating a gear re-engagement assembly implemented in the gantry to ensure correct meshing between an encoder gear and a gantry gear, in accordance with an aspect of the present disclosure.

FIG. 3 is a partial cutaway view of the gantry 12 illustrating the gear assembly 60 having the gear re-engagement assembly 61 implemented to ensure correct meshing and engagement of gears. The gear assembly 60 may include, among other components, a gantry gear 62, an encoder gear 64, and an encoder 66 enclosed by an encoder bracket 68. The encoder gear 64 is coupled to the encoder 66 (e.g., in a circumferential direction relative to the center of the rotation 24) and to the gantry gear 62 such that rotation of the gantry gear 62 drives rotation of encoder gear 64, and the encoder 66 is configured to track the rotation of the encoder gear 64 and to feed signal representing the rotational angle to the gantry motor controller 30 and/or the computer 36. It may be appreciated that the encoder gear 64 must properly mesh or engage with the gantry gear 62 (e.g., with teeth of the gantry gear 62, not shown) such that the rotational angle tracked by the encoder 66 may be used to make accurate termination of the gantry rotation and/or position. However, the encoder gear 64 may shift and become disengaged from the gantry gear 62 (e.g., jumping gear, skipping teeth, etc.) when subjected to sufficient vibrations (e.g., seismic event). To block the encoder gear 64 from losing its valuable positioning, the gear assembly 60 includes the gear re-engagement assembly 61 coupled to the encoder bracket 68 to ensure proper gear meshing or engagement between the encoder gear 64 and the gantry gear 62. It should also be noted while only one gantry gear 62 is shown in the illustrated embodiment, the gantry 12 may include one or more gantry gears and/or gantry gear assemblies.

In the illustrated embodiment, the gear re-engagement assembly 61 is fully enclosed within the enclosure 13 and does not contact the enclosure 13 during normal operation of the CT imaging system 10. The gear re-engagement assembly 61 includes a biasing bracket (or spring) 90 and a counter weight 91 configured to couple to the biasing bracket and to the encoder bracket 68 via any suitable removable coupling or fastening mechanism such as nuts, bolts, and screws. For example, the biasing bracket 90 and the counter weight 91 are both coupled to the encoder bracket 68, extending from the encoder 66. For example, the biasing bracket 90 and the counter weight 91 are both coupled to the encoder bracket 68 via one or more fasteners extending from the biasing bracket 90 through the counter weight 91 to the encoder bracket 68. As such, the gear re-engagement assembly 61 is connected to the encoder 66 and may move with the encoder 66 if the encoder gear 64 become disengaged from the gantry gear 62 (e.g., due to vibrations, seismic event). It should be noted that the biasing bracket 90 may have certain physical properties (e.g., dimensions, shape) and/or material properties (e.g., stiffness, force-deflection properties, bending properties) such that the counter weight 91 coupled to the biasing bracket 90 serves as a way to spring-load the biasing bracket 90.

The biasing bracket 90 includes a first portion 92, a second portion 94, and a transition portion 98. The first portion 92 is configured to be coupled to the counter weight 91 (e.g., via nuts, bolts, screws). The first portion 92 extends toward the enclosure 13 and transitions into the second portion 94, which is slightly tangential to the enclosure 13. The first portion 92 and the second portion 94 forms an angle 96 at the transition portion 98. The second portion 94 has a terminal portion 100, and the biasing bracket 90 is configured such that a clearance distance 102 exists between the terminal portion 100 and the enclosure 13 when the encoder gear 64 and the gantry gear 62 are correctly engaged. For example, the terminal portion 100 is disposed at a distance 102 away from a wall or a bearing bracket of the enclosure 13.

In operation, the biasing bracket 90 (e.g., the terminal portion 100) does not contact the enclosure 13 when the encoder gear 64 and the gantry gear 62 are properly meshed or engaged. However, if the encoder gear 64 becomes disengaged from the gantry gear 62 (e.g., the encoder gear 66 moves away from the gantry gear 62 and toward the enclosure 13 due to vibration), the biasing bracket 90 (e.g., the terminal portion 100) may contact the enclosure 13 and exert an action force on the enclosure 13. For example, the action force may be in a radial direction, a tangential direction, or a combination thereof, with respect to the enclosure 13. Simultaneously, a reaction force, opposite to the action force, is exerted on the biasing bracket 90, forcing the gear re-engagement assembly 61 away from the enclosure 13 and toward the gantry gear 62, and the encoder gear 64 connected thereto, is forced back to correct engagement with the gantry gear 62.

The biasing bracket 90 may be made of any suitable material in any suitable dimensions or shapes such that the biasing bracket 90 may be spring-loaded with the counter weight 91 as to enhance the action force to re-engage the encoder gear 64. For example, the biasing bracket 90 may have a general shape of a flap or elongated geometry. For example, the biasing bracket 90 may be made of steel (e.g., low carbon steel, hardened steel), a metal alloy, a composite, or any other suitable materials. It may also be appreciated that because the biasing bracket 90 has such spring and/or force-deflection properties, when subjected to vibrations (e.g., seismic event), the biasing bracket 90 may become more stiff (e.g., smaller bending or deflection) when the vibration frequency is high. Such characteristic may also enhance the action force to re-engage the encoder gear 64 when the vibration is violent (e.g., high vibration frequency). It should be noted that the re-engagement mechanism set forth above only becomes active when the encoder gear 64 is disengaged from the gantry gear 62 (e.g., the clearance distance 102 is zero), and the gear re-engagement assembly 61 does not interfere normal operation of the CT imaging system 10 when the encoder gear 64 and the gantry gear 62 are properly engaged.

Figure 4:
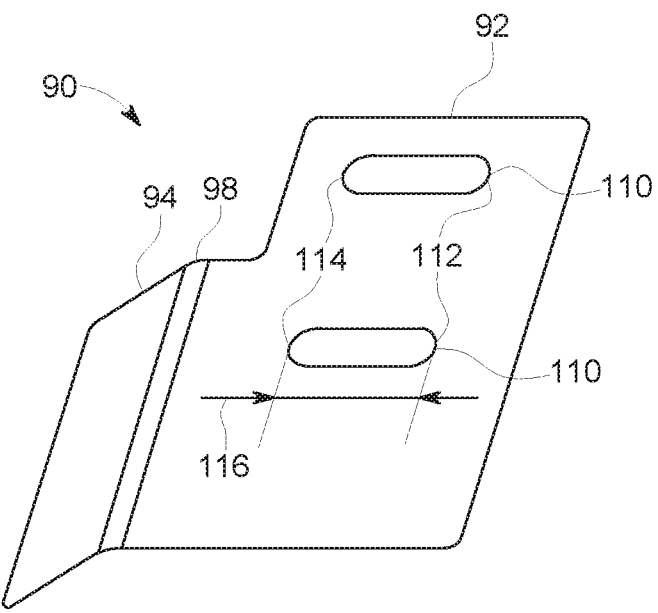
FIG. 4 is a perspective view of the gear re-engagement assembly of FIG. 3, in accordance with an aspect of the present disclosure.

Further details of the biasing bracket 90 may be appreciated with respect to FIG. 4, which is a perspective view of an embodiment of the biasing bracket 90. The biasing bracket 90 includes one or more elongated slots 110. Each slot 110 has two ends 112 and 114, and a longitudinal length 116 (e.g., between the ends 112 and 114). The one or more elongated slots 110 are configured to enable the biasing bracket 90 to be removably and adjustably coupled to the counter weight 91. Specifically, any suitable coupling or fastening mechanism (e.g., one or more nuts, bolts or screws) may be used to secure the biasing bracket 90 to the counter weight 91 at any locations along the longitudinal length 116 as to adjust the clearance distance 102. For example, a suitable coupling or fastening mechanism may secure the biasing bracket 90 at a location relatively closer to the end(s) 112, such that the biasing bracket 90 is adjusted toward to enclosure 13 to decrease the clearance distance 102. For example, a suitable coupling or fastening mechanism may secure the biasing bracket 90 at a location relatively closer to the end(s) 114, such that the biasing bracket 90 is adjusted away from to enclosure 13 to increase the clearance distance 102. In one embodiment, the clearance distance 102 may be approximately 2 millimeter (mm). In another embodiment, the clearance distance 102 may be any non-negative values and adjustable approximately within a range defined by the longitudinal length 116 of the one or more slots 110.

Figure 5:
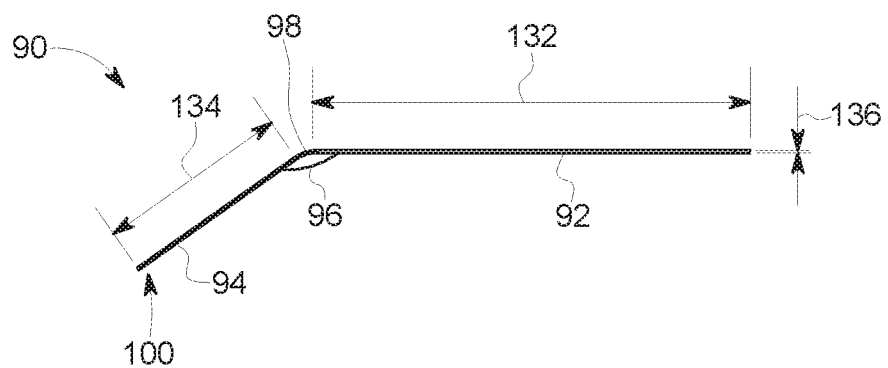
FIG. 5 is a front view of the gear re-engagement assembly of FIG. 3, in accordance with an aspect of the present disclosure.
Figure 6:
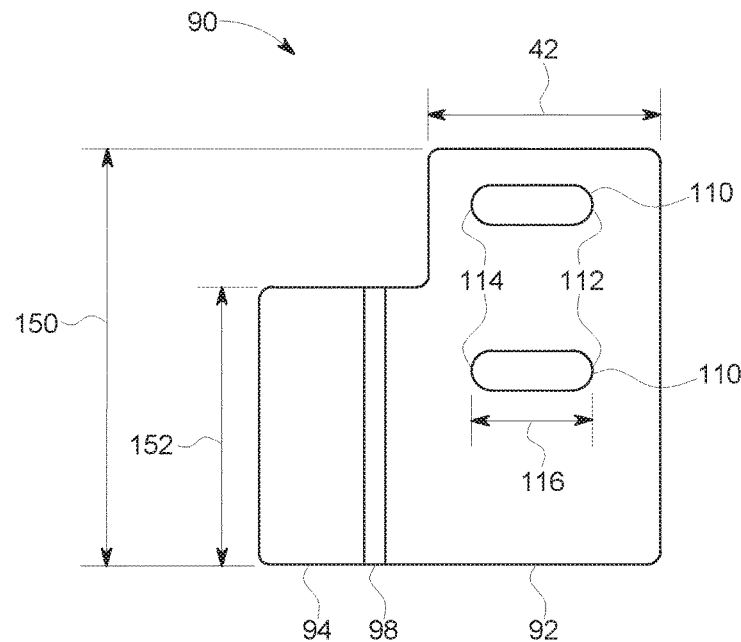
FIG. 6 is a top view of the gear re-engagement assembly of FIG. 3, in accordance with an aspect of the present disclosure.

Further details of the biasing bracket 90 may be appreciated with respect to FIGS. 5 and 6, which are a front view and a top view of the biasing bracket 90, respectively. As illustrated in FIG. 5, the biasing bracket 90 includes the first portion 92 having a length 132, the second portion 94 having a length 134, and the transition portion 98. The first, second, and the transition portions 92, 94, and 98 may have a generally constant thickness 136. In one embodiment, the biasing bracket 90 may have dimensions of the length 132 about 52 mm, the angle 96 about 145 degrees, the length 134 about 25 mm, and the thickness 136 about 0.4 mm. Alternatively, the dimensions (e.g., length, angle, thickness) may be any other suitable values. For example, the dimensions of the biasing bracket 90 may vary as to change the clearance distance 102 between the terminal portion 100 of the second portion 94 and the enclosure 13 of the gantry 12. While the first portion 92 and the second portion 94 of the biasing bracket 90 each may generally have any suitable geometry or shape, in the illustrated embodiment as shown in FIG. 6, the first and second portions 92, 94 each has a generally rectangular shape with deburred corners. Further, the first portion 92 may have a width 150, and the second portion 94 may have a width 152 smaller than the width 150. In one embodiment, the widths 150 and 152 may be around 75 mm and around 50 mm, respectively. Alternatively, the width 152 may be approximately equal to or greater than the width 150 depending on the configuration and/or fitting of the gear re-engagement assembly 61 within the enclosure 13.

Figure 7:
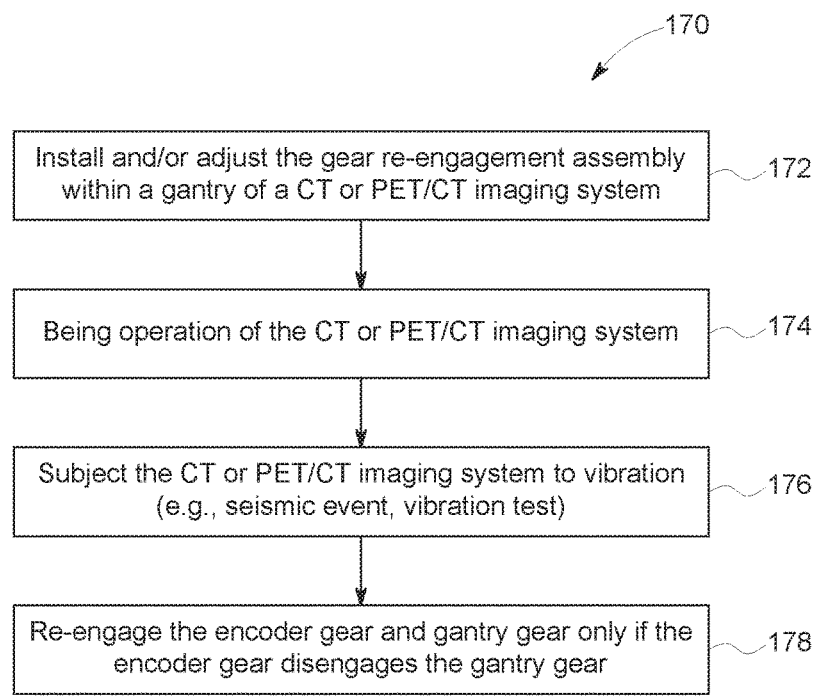
FIG. 7 is a flow chart illustrating a process for utilizing the gear re-engagement assembly, in accordance with an aspect of the present disclosure.

With the foregoing in mind, and turning now to FIG. 7, a flowchart is depicted setting forth a method 170 for utilizing the gear re-engagement assembly 61 in accordance with one embodiment of the present disclosure. In this method 170, the gear re-engagement assembly 61 is installed/adjusted within the gantry 12 of the CT or PET/CT imaging system 10 (block 172). For example, the gear re-engagement assembly 61 may be secured to the encoder bracket 68 through the one or more elongated slots 110 via nuts, bolts, screws or any other suitable coupling mechanism. For example, the relative position (e.g., relative to the gantry enclosure 13) of the gear re-engagement assembly 61 may be adjusted along the longitudinal length 116 (e.g., between the ends 112 and 114) of the one or more elongated slots 110 to increase or decrease the clearance distance 102.

In the depicted method 170, the CT or PET/CT imaging system 10 may begin operation once the gear re-engagement assembly 61 is installed/adjusted (block 174). For example, the CT or PET/CT imaging system 10 may proceed the operation and the gantry 12 may rotate about the center of rotation 24 to obtain scanning images. It should be noted that the gear re-engagement assembly 61 does not interfere with operation of the CT or PET/CT imaging system 10 when the encoder gear 64 and gantry gear 62 are correctly meshed or engaged.

The CT or PET/CT imaging system 10 may be subjected to vibration (block 176). For example, the CT or PET/CT imaging system 10 may experience vibration during a seismic event and/or a vibration test. Due to sufficient vibration, the encoder gear 64 may become disengaged from the gantry gear 62. In this case, the gear re-engagement assembly 61 may re-engage the encoder gear 64 and the gantry gear 62 by forcing the encoder gear 64 back to correct engagement with the gantry gear 62 (block 78). For example, in an event that the encoder gear 64 becomes disengaged and displaced from the gantry gear 62, the biasing bracket 90 of the gear re-engagement assembly 61 contacts the enclosure 13 of the gantry 12 and exerts an action force (e.g., spring-loaded force by the counter weight 91) on the enclosure 13. Simultaneously, a reaction force, opposite to the action force, is exerted on the biasing bracket 90, forcing the gear re-engagement assembly 61 away from the enclosure 13 and toward the gantry gear 62, and the encoder gear 64 connected thereto, is forced back to correct engagement with the gantry gear 62. As such, the gear re-engagement process occurs automatically and only if the encoder gear 64 disengages the gantry gear 62.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimesd is:

1. An X-ray imaging system, comprising:
   a gantry, rotatable about an axis of rotation;
   a radiation source mounted on the gantry and configured to emit radiation; and
   one or more detectors configured to detect the emitted radiation, wherein the gantry comprises:
      a gear assembly coupled to a motor to enable rotation of the gantry, wherein the gear assembly comprises a gantry gear;
      an encoder for detecting position of the gantry, wherein the encoder comprises an encoder gear meshed with the gantry gear; and
      a gear re-engagement assembly configured to couple to the encoder and to force the encoder gear into correct engagement with the gantry gear when the encoder gear becomes disengaged from the gantry gear.

2. The X-ray imaging system of claim 1 comprises a computed tomography (CT) system or a position emission tomography and CT combined (PET/CT) system.

3. The X-ray imaging system of claim 1, wherein the gear re-engagement assembly comprises:
   a counter weight coupled to the encoder; and
   a biasing member coupled to and spring-loaded by the counter weight, wherein the biasing member comprises a first portion configured to be adjustably coupled to the counter weight, and a second portion that has a terminal portion that is disposed at a clearance distance away from a wall of the gantry.

4. The X-ray imaging system of claim 3, wherein the clearance distance is approximately two millimeters when the encoder gear is correctly engaged with the gantry gear.

5. The X-ray imaging system of claim 3, wherein when the encoder gear becomes disengaged from the gantry gear, the biasing member of the re-engagement assembly contacts the wall of the gantry and forces the encoder gear into correct engagement with the gantry gear.

6. The X-ray imaging system of claim 3, wherein the clearance distance is adjustable by adjusting coupling between the first portion and the counter weight.

7. The X-ray imaging system of claim 3, wherein the first portion comprises one or more elongated slots that enable the first portion to be adjustably coupled to the counter weight.

8. The X-ray imaging system of claim 3, wherein the biasing member of the re-engagement assembly is made of steel, metal alloy, or composite.

9. The X-ray imaging system of claim 3, wherein an angle between the first portion and the second portion of the biasing member is approximately 145 degrees.

10. A gear re-engagement system for a gantry of an X-ray imaging system, comprising:
    a biasing member; and
    a counter weight coupled to the biasing member, wherein the counter weight is configured to spring load the biasing member, and the counter weight is configured to couple to an encoder within the gantry and to force an encoder gear into correct engagement with a gantry gear within the gantry when the encoder gear becomes disengaged from the gantry gear.

11. The gear re-engagement system of claim 10, wherein when the encoder gear becomes disengaged from the gantry gear, the biasing member is configured to contact a wall of the gantry and to force the encoder gear into correct engagement with the gantry gear.

12. The gear re-engagement system of claim 10, wherein the biasing member comprises a first portion configured to be adjustably coupled to the counter weight, and a second portion that forms an angle with the first portion and has a terminal portion, which is configured to be disposed at a clearance distance from a wall of the gantry.

13. The gear re-engagement system of claim 12, wherein the clearance distance is adjustable by adjusting coupling between the first portion and the counter weight.

14. The gear re-engagement system of claim 12, wherein the clearance distance is approximately two millimeters when the encoder gear is correctly engaged with the gantry gear.

15. The gear re-engagement system of claim 12, wherein the angle between the first portion and the second portion of the biasing member is approximately 145 degrees.

16. The gear re-engagement system of claim 12, wherein the first portion comprises one or more elongated slots that enable the first portion to be adjustably coupled to the counter weight.

17. A method for correcting gear jumping in a gantry of an X-ray imaging system comprising:
    coupling a gear re-engagement assembly to an encoder within an enclosure of the gantry;
    rotating the gantry about an axis of rotation based on a motor-driven gear assembly, comprising a gantry gear, wherein the gantry gear is correctly engaged with an encoder gear of the encoder;
    subjecting the gantry to vibration such that the encoder gear becomes disengaged from the gantry gear; and forcing the disengaged encoder gear into correct engagement with the gantry gear via the gear re-engagement assembly by contacting a spring-loaded biasing member of the gear re-engagement assembly with a wall of the enclosure.

18. The method of claim 17, wherein coupling the gear re-engagement assembly to the encoder comprises adjustably coupling the spring-loaded biasing member to a counter weight of the gear re-engagement assembly, wherein the counter weight is configured to load the spring-loaded biasing member, and the counter weight is configured to couple to the encoder within the gantry.

19. The method of claim 18, wherein the spring-loaded biasing member comprises one or more elongated slots to enable adjustably coupling the spring-loaded biasing member to the counter weight.

20. The method of claim 19, comprising adjusting a clearance distance between the spring-loaded biasing member and the wall of the enclosure by adjusting a position of the spring-loaded biasing member relative to the counter weight.

\* \* \* \* \*